United States Patent [19]

Wu

[11] 4,282,382

[45] Aug. 4, 1981

[54] PRODUCTION OF CYCLOHEXYLBENZENE HYDROPEROXIDE

[75] Inventor: Yulin Wu, Bartlesville, Okla.

[73] Assignee: Phillips Petroleum Company, Bartlesville, Okla.

[21] Appl. No.: 54,081

[22] Filed: Jul. 2, 1979

[51] Int. Cl.³ ............................................. C07C 179/03
[52] U.S. Cl. ..................................... 568/570; 568/573
[58] Field of Search ........................ 568/570, 573, 574

[56] References Cited

U.S. PATENT DOCUMENTS

| | | | |
|---|---|---|---|
| 2,615,921 | 10/1952 | Dougherty et al. | 568/570 |
| 2,751,417 | 6/1956 | Enos et al. | 568/570 |
| 2,790,004 | 4/1957 | Dougherty | 568/570 |
| 2,798,096 | 7/1957 | Baumgarter | 568/570 |

*Primary Examiner*—Werren B. Lone

[57] ABSTRACT

A process for preparation of cyclohexylbenzene hydroperoxide comprising reacting cyclohexylbenzene with oxygen in a diluent consisting essentially of cyclohexane under conditions suitable for converting said cyclohexylbenzene to cyclohexylbenzene hydroperoxide.

13 Claims, No Drawings

PRODUCTION OF CYCLOHEXYLBENZENE HYDROPEROXIDE

This invention relates to the production of cyclohexylbenzene hydroperoxide by the oxidation of cyclohexylbenzene.

The oxidation of cyclohexylbenzene to cyclohexylbenzene hydroperoxide is a well-known reaction. Cyclohexylbenzene hydroperoxide is of interest because its acid catalyzed cleavage results in the production of phenol and cyclohexanone.

The oxidation of cyclohexylbenzene in the absence of a diluent has been found to be undesirable because at higher cyclohexylbenzene conversions, the selectivity to the hydroperoxide decreases. In addition, as the cyclohexylbenzene conversion approaches about 25 weight percent, the solution viscosity increases and the heat transfer properties become worse, thus increasing the possibility of localized overheating, hydroperoxide decomposition, and explosion.

The use of diluents for the oxidation of cyclohexylbenzene frequently results in a decrease in the rate of oxidation. Since cyclohexylbenzene has a relatively low oxidation rate compared with, for example, cumene, some diluents are oxidized faster than the cyclohexylbenzene and form products that would complicate product separation and purification.

An object of the invention is to provide a process for the oxidation of cyclohexylbenzene to cyclohexylbenzene hydroperoxide with good cyclohexylbenzene conversions while maintaining high selectivities to the hydroperoxide.

Another object of the present invention is to provide a process for the oxidation of cyclohexylbenzene to cyclohexylbenzene hydroperoxide in the presence of a diluent which does not result in oxidation products which complicate separation and purification of desired production.

In accordance with the instant invention cyclohexylbenzene is reacted with oxygen in a diluent consisting essentially of cyclohexane under conditions suitable for converting said cyclohexylbenzene to cyclohexylbenzene hydroperoxide.

In the process of this invention cyclohexylbenzene (I) is oxidized in the presence of cyclohexane to form cyclohexylbenzene hydroperoxide (II). A subsequent acid catalyzed cleavage of II yields the desirable products phenol (III) and cyclohexanone (IV).

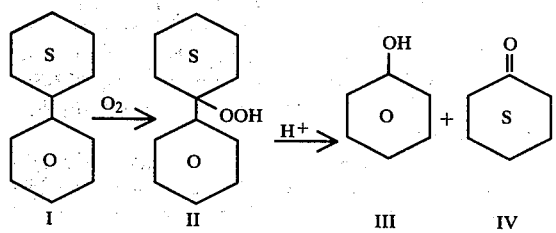

In accordance with the instant invention, the cyclohexane is partially oxidized under the reaction conditions to cyclohexanone (IV), cyclohexanol (V), and cyclohexane hydroperoxide (VI).

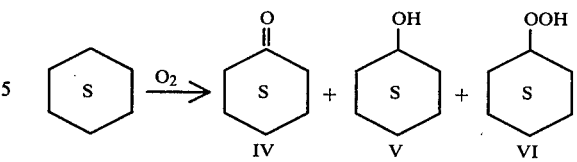

Of the products from the oxidation of cyclohexane, cyclohexanone (IV) is one of the products obtained from the acid catalyzed cleavage of cyclohexylbenzene hydroperoxide. Cyclohexanol (V) recovered from the acid cleavage step can be dehydrogenated using known techniques to cyclohexanone. Cyclohexane hydroperoxide can be converted by acid cleavage step or oxidation to cyclohexanone and cyclohexanol. Thus, the oxidation products resulting from the oxidation of the cyclohexane diluent assist rather than complicate the recovery of desirable products from the cyclohexylbenzene hydroperoxide product.

OXIDATION MIXTURE

The oxidation reaction of the present invention is carried out in a reaction mixture containing cyclohexylbenzene and cyclohexane. The cyclohexylbenzene can be prepared by any suitable method, but is preferably prepared by the hydroalkylation of benzene. Cyclohexylbenzene will generally be present in the reaction mixture in amounts in the range from about 1 to about 95 weight percent and preferably in the range from about 5 to about 70 weight percent. The percentages are based on the combined weight of the cyclohexane and the cyclohexylbenzene.

Cyclohexane is utilized in the reaction of this invention as a diluent and as a co-oxidant. The cyclohexane used generally contains greater than about 95 weight percent cyclohexane. Other materials, such as benzene, can be present in the cyclohexane if these materials are substantially inert under the reaction conditions. The amount of cyclohexane in the reaction mixture will be broadly from about 5 to about 99 weight percent, preferably from about 30 to about 95 weight percent. The percentages are based on the weight of the combined weights of the cyclohexane and the cyclohexylbenzene.

Although not required in the present invention, various initiators, generally hydroperoxides such as cyclohexylbenzene hydroperoxide can be present to reduce the induction period. The initiator is generally present in the range of from about 0.1 to about 5 weight percent with the percentage based on the weight of the cyclohexylbenzene present.

Although not required by the present invention, it is advantageous to carry out the reaction in the presence of small amounts of basic metal salts, oxides, or hydroxides. The use of basic materials to neutralize acidic compounds formed during the reaction is known in the art. The carbonates, hydroxides, and acetates of the alkali metals, and the oxides and hydroxides of alkaline earth metals are suitable basic materials. Examples include sodium hydroxide, sodium carbonate, sodium acetate, magnesium oxide, and the like. The basic material will normally be present as an aqueous solution in the range of about 0.01 to about 1 weight percent with the percentage based on the weight of the cyclohexylbenzene.

In addition, oxidation catalysts can be utilized if desired. Known catalysts include metallic silver, and silver salts (see, for example, U.S. Pat. No. 2,820,832). The catalyst will generally be present in amounts in the range of about 0.01 to about 2 weight percent with the percentage based on the weight of the cyclohexylbenzene present in the reaction mixture.

II. REACTION CONDITIONS

In its broadest aspect the present invention can be carried out under any conditions suitable for converting cyclohexylbenzene to cyclohexylbenzene hydroperoxide. Generally, the temperatures utilized in the reaction of this invention range from about 50° to about 160° C. and preferably range from about 100° to about 140° C. Generally, the pressure can range from atmospheric to about 1000 psig (6894 kPa) at the reaction temperature.

The amount of oxygen employed for the oxidation reaction can be expressed in terms of the mole ratio of oxygen to cyclohexylbenzene. This ratio is broadly from about 0.005/1 up to about 20/1 and even higher and preferably from about 0.001/1 to about 10/1. The oxygen can be introduced into the reaction zone in any convenient manner. Air as well as other mixtures of gases substantially inert under the reaction conditions with oxygen may be utilized as a source of oxygen. Essentially pure oxygen can also be utilized.

The oxidation reaction of this invention can be carried out in any batch or continuous reactor that is capable of withstanding the pressures and oxidizing conditions which are present. Stirring or mixing by conventional means will be helpful, but is not regarded as necessary.

The oxidation reaction of this invention is generally carried out for a time period sufficient to obtain the desired degree of cyclohexylbenzene conversion. For cyclohexane levels below about 50 weight percent, the cyclohexylbenzene conversion should preferably be in the range of about 20 to about 25 weight percent. Higher conversions have been found to result in lower selectivities to the hydroperoxide. For cyclohexane levels above about 50 weight percent, the cyclohexylbenzene conversion is advantageously in the range from about 25 to about 35 weight percent. The above cyclohexane percentages are based on the combined weight of the cyclohexane and the cyclohexylbenzene. The conversions can be estimated by oxygen consumption or by periodic iodometric titrations of reaction mixture aliquots. In addition, samples of the reaction mixture can be taken periodically from the reaction mixture for gas-liquid chromatographic analysis.

III. REACTION PRODUCT WORKUP

At the conclusion of the oxidation reaction time period, the reaction mixture can be cooled, depressured, and the cyclohexane removed by distillation. The cyclohexane can be recycled to the oxidation reaction is desired. If a base was utilized in the oxidation reaction, the mixture can be neutralized with an acid such as sulfuric acid. The reaction mixture can then be passed to an acid cleavage step. During the acid cleavage, the cyclohexylbenzene hydroperoxide will be converted to phenol and cyclohexanone and the cyclohexane hydroperoxide will be converted to cyclohexanone and cyclohexanol. The acid cleavage step is a well-known reaction using strong acids such as sulfuric acid.

The acid cleavage mixture can be separated by conventional techniques including fractional distillation, liquid-liquid extraction, and extractive distillation. Cyclohexanol will, depending on the particular separation scheme chosen, generally be obtained by itself or in combination with cyclohexanone. In either case, the cyclohexanol can be dehydrogenated to cyclohexanone. Numerous methods of cyclohexanol dehydrogenation are known and many of these are discussed in "Cyclohexane, Cyclohexanol, and Cyclohexanone" S. A. Miller, Chemical and Process Engineering, June 1969, pp. 63–72.

IV. PRODUCT UTILITY

As previously discussed, the ultimate products of the oxidation of cyclohexylbenzene followed by an acid cleavage of the hydroperoxide are phenol and cyclohexanone. The final products of cyclohexane from the oxidation step and the acid cleavage step are cyclohexanone and cyclohexanol.

Phenol is a large volume chemical useful as a disinfectant and in the manufacture of resins, medical and industrial organic compounds, and dyes. Cyclohexanone is useful as a solvent for various materials and as an intermediate in the production of adipic acid for use in nylon 6,6. Cyclohexanol is useful as a solvent or can be converted to cyclohexanone.

The process of this invention could be very advantageously utilized in conjunction with a plant in which cyclohexylbenzene is produced from benzene by hydroalkylation because cyclohexane is a byproduct of the hydroalkylation. Thus such a plant would produce both the reactant and the diluent.

The present invention will be further illustrated by the following examples.

The runs in the following examples were all carried out in a 300 ml. stainless steel autoclave that was equipped with a pressure gauge, thermocouple, and magnetic stirrer. In each run, the cyclohexylbenzene, any diluent or co-oxidant, an initiator (cyclohexylbenzene hydroperoxide-about 1 weight percent of the weight of cyclohexylbenzene), and in some runs, aqueous sodium hydroxide (less then 1 weight percent of the cyclohexylbenzene weight) was charged to the autoclave. The reactor was pressured to about 200 psig (1379kPa) with oxygen and heated to the reaction temperature (normally 130° to 135° C.). The reaction mixture was heated with stirring for the desired reaction time period with the extent of reaction being monitored by the decrease in oxygen pressure.

At the conclusion of the reaction time period, the reaction mixture was cooled and depressured. The reaction mixture was analyzed for the total hydroperoxide content by iodometric titration and analyzed by gas-liquid chromatography (glc) for the amounts of cyclohexylbenzene, cyclohexanone (if formed), and cyclohexanol (if formed). The reaction mixture was then treated with triphenylphosphine to convert the hydroperoxides to alcohols. A glc analysis of the treated mixture was used to determine the amounts and identity of the alcohols and, therefore, of the precursor hydroperoxides. The glc peak areas were converted to weights using an internal standard.

The cyclohexylbenzene used in the runs was prepared by the hydroalkylation of benzene. The cyclohexane was pure grade (>99 mole percent purity) from Phillips Petroleum Company.

EXAMPLE I

A series of control runs was carried out in which cyclohexylbenzene (CHB) was oxidized to cyclohexylbenzene hydroperoxide with either no added diluent or with ethylbenzene or toluene as diluent. The results are presented in Table I.

TABLE I

| Run No. | CHB Wt., g. | Diluent, | g. | Diluent Wt. %[a] | Run Time, Hrs. | Run Temp., °C. | CHB Conv. Wt. % | Selectivity[b] Wt. % |
|---|---|---|---|---|---|---|---|---|
| 1 | 97.6 | none, | 0 | 0 | 2 | 130° | 14 | 72 |
| 2 | 63 | none, | 0 | 0 | 3 | 130° | 17 | 79 |
| 3[c] | 97.4 | none, | 0 | 0 | 4 | 127° | 19 | 84 |
| 4[c] | 97.4 | none, | 0 | 0 | 5 | 132° | 43 | 54 |
| 5 | 35 | $C_6H_5CH_2CH_3$, | 35 | 50 | 4.2 | 130° | 12 | 93 |
| 6 | 15 | $C_6H_5CH_2CH_3$, | 45 | 75 | 4.5 | 130° | 10 | 96 |
| 7 | 30 | $C_6H_5CH_3$, | 30 | 50 | 7 | 130° | 12 | 99 |
| 8 | 30 | $C_6H_5CH_3$, | 30 | 50 | 7 | 135° | 22 | 88 |

[a]Weight % of the total mixture of CHB and diluent.
[m]Selectivity to cyclohexylbenzene hydroperoxide based on the amount of cyclohexylbenzene reacted.
[c]0.624 g of aqueous NaOH (50 weight % NaOH) was present.

The results in Table I demonstrate the difficulties encountered with the oxidation of cyclohexylbenzene without an added diluent or with diluents such as ethylbenzene or toluene. Runs 1 to 4 were carried out without an added diluent. At higher conversions (run 4) the selectivity to cyclohexylbenzene hydroperoxide has decreased from the values obtained at lower conversions (runs 1, 2, 3).

Runs 5 and 6 were carried out with ethylbenzene as a diluent. Although selectivities to cyclohexylbenzene hydroperoxide were high at these CHB conversions, significant amounts of ethylbenzene hydroperoxide were formed during the oxidation. Since the presence of the ethylbenzene hydroperoxide would complicate the later acid cleavage step and product separation, the use of ethylbenzene as a diluent for the oxidation of cyclohexylbenzene is undesirable.

Runs 7 and 8 were carried out with toluene as a diluent. Both runs were very slow. The runs show a high selectivity to cyclohexylbenzene hydroperoxide at low conversion at 130° C. (run 7) and a lower selectivity to cyclohexylbenzene hydroperoxide at higher conversions at 135° C. (run 8). The slow reaction rate makes toluene an undesirable diluent for the oxidation of cyclohexylbenzene.

EXAMPLE II

A series of runs was carried out to demonstrate the oxidation of cyclohexylbenzene (CHB) to cyclohexylbenzene hydroperoxide in cyclohexane at 130° C. The results of these runs are summarized in Table II.

TABLE II

| Run No. | CHB Wt., g | Cyclohexane g. Wt. %[a] | | Run Time, Hrs. | CHB Conv. Wt. % | Selectivity,[b] Wt. % |
|---|---|---|---|---|---|---|
| 9 | 79 | 10 | 11 | 3 | 14 | 99 |
| 10 | 61 | 20 | 25 | 3.6 | 18 | 92 |
| 11 | 52 | 25 | 32 | 5.8 | 37 | 60 |
| 12 | 40 | 20 | 33 | 4.8 | 24 | 85 |
| 13 | 42 | 30 | 41 | 6.2 | 30 | 62 |
| 14[c] | 30 | 30 | 50 | 5.4 | 28 | 78 |
| 15[d] | 20 | 40 | 67 | 3.5 | 32 | 88 |

[a]Weight % cyclohexane based on the combined cyclohexane-cyclohexylbenzene weight.
[b]Selectivity to cyclohexylbenzene hydroperoxide based on the weight of cyclohexylbenzene reacted.
[c]3 drops of 50 weight % aqueous NaOH were present.
[d]1 drop of 50 weight % aqueous NaOH was present.

The results of runs 9, 10, 12, 14, and 15 in Table II demonstrate the process of the present invention for the oxidation of cyclohexylbenzene to the corresponding hydroperoxide in the presence of a wide range of levels of cyclohexane. This oxidation can be carried to good cyclohexylbenzene conversions while maintaining good selectivities to the cyclohexylbenzene hydroperoxide.

Runs 11 to 13 show that the selectivity to cyclohexylbenzene hydroperoxide is decreased when the cyclohexylbenzene conversion is greater than the preferred amounts taught by the present invention. For example, for cyclohexane levels below about 50 weight percent, cyclohexylbenzene conversions should be between about 20 and about 25 percent. Runs 11 and 13 were carried to cyclohexylbenzene conversions of 37 and 30 percent and the selectivities to the hydroperoxide were around 60 percent. For comparison, run 12 was carried out to a cyclohexylbenzene conversion of 24 percent and the selectivity to the cyclohexylbenzene hydroperoxide was 85 percent.

The oxidation reactions in the runs in Table II resulted in the oxidation of a portion of the cyclohexane. For example, in run 14, about 5.5 weight percent of the cyclohexane was oxidized. An analysis of the product mixture showed that cyclohexanone, cyclohexanol, and cyclohexane hydroperoxide were present.

What is claimed is:

1. A process for preparation of cyclohexylbenzene hydroperoxide comprising reacting cyclohexylbenzene with oxygen in a diluent consisting essentially of cyclohexane under conditions suitable for converting said cyclohexylbenzene to cyclohexylbenzene hydroperoxide.

2. A process according to claim 1 wherein the temperature of said reaction is in the range of about 50° C. to about 160° C., the pressure of said reaction is in the range of atmospheric to about 1000 psig, and the mole ratio of oxygen to cyclohexylbenzene is in the range of about 0.005/1 to 20/1.

3. A process according to claim 2 wherein the amount of cyclohexane in the reaction mixture is in the range of about 5 to about 99 weight percent of the combined weights of the cyclohexane and the cyclohexylbenzene.

4. A process according to claim 3 wherein the temperature of said reaction is in the range of about 100° C. to about 140° C.

5. A process according to claim 4 wherein the amount of cyclohexane in the reaction mixture is in the range of about 30 to about 95 weight percent of the combined weights of the cyclohexane and the cyclohexylbenzene.

6. A process according to claim 5 wherein the amount of cyclohexane in the reaction mixture is below about 50 weight percent of the combined weight of the cyclohexane and the cyclohexylbenzene and wherein the reaction is carried out for a time sufficient to obtain conversion of about 20 to about 25 weight percent of said cyclohexylbenzene.

7. A process according to claim 6 wherein said reaction is carried out in the presence of a basic material selected from the group consisting of the carbonates, hydroxides, and acetates of alkali metals and the oxides and hydroxides of alkaline earth metals and the amount of said basic material is in the range of about 0.01 to about 1 weight percent of the weight of the cyclohexylbenzene.

8. A process according to claim 5 wherein the amount of cyclohexane in the reaction mixture is above about 50 weight percent of the combined weights of the cyclohexane and the cyclohexylbenzene and wherein the reaction is carried out to obtain conversion of about 25 to about 35 weight percent of the cyclohexylbenzene.

9. A process according to claim 8 wherein said reaction is carried out in the presence of a basic material selected from the group consisting of the carbonates, hydroxides, and acetates of alkali metals and the oxides and hydroxides of alkaline earth metals and the amount of said basic material is in the range of about 0.01 to about 1 weight percent of the weight of the cyclohexylbenzene.

10. A process according to claim 3 wherein the amount of cyclohexane in the reaction mixture is below about 50 weight percent of the combined weight of the cyclohexane and the cyclohexylbenzene and wherein the reaction is carried out for a time sufficient to obtain conversion of about 20 to about 25 weight percent of said cyclohexylbenzene.

11. A process according to claim 10 wherein said reaction is carried out in the presence of a basic material selected from the group consisting of the carbonates, hydroxides, and acetates of alkali metals and the oxides and hydroxides of alkaline earth metals and the amount of said basic material is in the range of about 0.01 to about 1 weight percent of the weight of the cyclohexylbenzene.

12. A process according to claim 3 wherein the amount of cyclohexane in the reaction mixture is above about 50 weight percent of the combined weights of the cyclohexane and the cyclohexylbenzene and wherein the reaction is carried out to obtain conversion of about 25 to about 35 weight percent of the cyclohexylbenzene.

13. A process according to claim 12 wherein said reaction is carried out in the presence of a basic material selected from the group consisting of the carbonates, hydroxides, and acetates of alkali metals and the oxides and hydroxides of alkaline earth metals and the amount of said basic material is in the range of about 0.01 to about 1 weight percent of the weight of the cyclohexylbenzene.

* * * * *